United States Patent

Faccioli et al.

[11] Patent Number: 5,984,971
[45] Date of Patent: Nov. 16, 1999

[54] PROSTHESIS FOR METACARPAL-PHALANGEAL AND INTERPHALANGEAL JOINTS IN HANDS OR FEET

[75] Inventors: Giovanni Faccioli, Monzambano; Renzo Soffiatti, Nogara; Maurizio Petrolati, Legnano; Giorgio Delaria, Castellanza; Gianrico Abbiati, Cantalupo di Cerro Maggiore, all of Italy

[73] Assignee: Tecres S.p.A., Verona, Italy

[21] Appl. No.: 08/894,333

[22] PCT Filed: Feb. 15, 1996

[86] PCT No.: PCT/EP96/00670

§ 371 Date: Dec. 5, 1997

§ 102(e) Date: Dec. 5, 1997

[87] PCT Pub. No.: WO96/25129

PCT Pub. Date: Aug. 22, 1996

[30] Foreign Application Priority Data

Feb. 17, 1995 [IT] Italy ................................. VR95A0012

[51] Int. Cl.$^6$ .................................. A61F 2/42; A61F 2/30
[52] U.S. Cl. ................................................. 623/21; 623/18
[58] Field of Search .................................. 623/18, 20, 21

[56] References Cited

U.S. PATENT DOCUMENTS

| | | |
|---|---|---|
| 3,466,669 | 9/1969 | Flatt . |
| 3,992,726 | 11/1976 | Freeman et al. .................. 623/21 |
| 4,204,284 | 5/1980 | Koeneman . |

FOREIGN PATENT DOCUMENTS

| | | |
|---|---|---|
| 0278184 | 8/1988 | European Pat. Off. . |
| 0280424 | 8/1988 | European Pat. Off. . |
| 1105159 | 11/1955 | France . |
| 2219303 | 12/1989 | United Kingdom . |
| 9104718 | 4/1991 | WIPO . |
| 9107149 | 5/1991 | WIPO . |

*Primary Examiner*—Mickey Yu
*Assistant Examiner*—Dinh X. Nguyen
*Attorney, Agent, or Firm*—Hopgood, Calimafde, Kalil & Judlowe, LLP

[57] ABSTRACT

A metacarpal-phalangeal and/or interphalangeal (1) prosthesis, particularly for joints in the hand or foot, comprising a pair of pins (2, 3) which can be implanted in bone adjacent to a joint to be restored and connected by a flexible joint (4) encapsulated in a protective enclosure formed from the same biocompatible material as the pins. The biocompatible material may be a mixture of plastic resins having high compatibility. The enclosure comprises a pair of half shells (5, 6)integral with the corresponding pins which extend axially on opposite side of a longitudinal plane of symmetry (S) which perpendicularly intersects the axis of rotation (a) of the joint. In a first embodiment, axis (a) is defined by a cylindrical pin (13) inserted in the axial cavity in the half shells and free to rotate with respect to at least one axis with limited flexibility in a plane perpendicular to the axis of rotation (a). In a second embodiment the pin (13) is replaced by a cylindrical (13') or hemispherical (13") extension of one of the pins. Axis (a) may be defined by a helicoidal spring (14, 17) or by axial elastic wires (23, 24) anchored in the pins with transverse end plates (25, 26).

17 Claims, 3 Drawing Sheets

PROSTHESIS FOR METACARPAL-PHALANGEAL AND INTERPHALANGEAL JOINTS IN HANDS OR FEET

FIELD OF APPLICATION

This invention relates to a metacarpal-phalangeal or interphalangeal prosthesis, especially for joints in the hands and feet.

Where a finger or toe is lost or its functional performance is compromised as a result of injury, impact, rheumatoid arthritis, osteoarthritis, post-traumatic or post-infective osteoarthritis, modern surgical techniques make it possible to replace the natural joint with an artificial joint which is located between the metacarpal bone and the phalanges or between adjacent phalanges.

STATE OF THE ART

Some types of phalangeal prosthesis which generally comprise a joint connecting two pins which can each be implanted in the metacarpal bone and/or phalanges have been in use for many years.

The pins may be constructed of rigid materials, for example steel, titanium, carbon, or using soft materials, such as resins or silicone rubbers.

In the latter case, first introduced in the 70s by Swanson, the pins are joined together by a unitary connecting member with a transverse depression which encourages elastic flexion of the joint and rotation of the pins. Although this type of joint is aesthetically very satisfactory and provides an appreciable range of movement, it has some short term disadvantages, such as complete flipping of the joint and excessive movement in a lateral plane, and in the long term progressive disintegration of the bone and stiffening of the joint.

In metal prostheses the pins may be bare or coated with biocompatible material, such as hydroxyapatite. A disadvantage of these prostheses is their tendency to release metals which enter into the blood circulation and can cause metal intoxication. A further disadvantage arises from the high cost of the basic material, which may be extremely rare, such as titanium.

In rigid prostheses the joints are hinge or ball joints, and may be provided with elastic members, and have the disadvantage that they can stiffen in the course of time and cause infections, as they are in contact with bone and connective tissues.

U.S. Pat. No. 4,204,284 discloses a finger joint prosthesis comprising two pins and a flexible joint with the pins being made of biocompatible material (see column 4 lines 45–column 6 line 15; FIGS 1 and 2).

EP-A-280424 discloses a finger joint endoprostheses and it mentions as being advantageous to employ compatible materials and in the detailed examples reference is made to one and the same material being used for all the components such as protective caps etc. (see column 3, line 53–column 4–line 4).

This invention is intended to eliminate or at least reduce the above mentioned disadvantages by providing a rigid pin endoprothesis which permits easy implantation without any risks of incompatibility or infection, such as to guarantee mobility in the joint over a period of time.

The invention accomplishes these objects by the provision of a metacarpal-phalangeal or interphalangeal prosthesis, particularly for joints in the hand or foot, comprising two pins (2, 3) which can be inserted into bone adjacent to a joint to be restored, and a flexible joint (4) or coupling designed to join the said pins to each other, said pins (2, 3) being constructed of a material which is biocompatible with the surrounding tissue, said joint (4) being encapsulated in a protective enclosure, characterized in that said enclosure is formed of the same basic material as the pins (2, 3) and comprises a pair of opposing half shells (5, 6) integral with the corresponding pins (2, 3).

Because of the fact that the pins and the enclosure for the pins are formed of the same basic material as the pins and the layer covering the joint, the endoprosthesis according to the invention guarantees absolutely stable and durable anchoring in the bone, with minimum risk of infection or rejection.

Preferably the biocompatible material is a hardening plastic resin with high compatibility.

Preferably, the material forming the said pins and the said enclosure is a bone cement mixture, for example comprising a solid phase of polymethyl methacrylate polymer combined with a liquid phase of monomethyl methacrylate monomer to form a hardenable plastic resin.

The pair of opposing half-shells, integral with the corresponding pins, extend on opposite sides with respect to a longitudinal plane of symmetry which is substantially perpendicular to the axis of rotation of the joint.

In a first preferred embodiment the half shells have a substantially cylindrical shape with an axial cavity and a transverse base wall, and the axis of rotation of the joint is defined by a pin inserted in the axial cavity of the half shells in such a way as to rotate freely with respect to at least one of them with a predetermined play.

In a second embodiment the axis of rotation is defined by a helicodal spring placed within the said hollow connecting members.

As a result of the material forming the pins and the protective enclosure for the joint, absolute biocompatability and stability of the endoprosthesis in its implanted location is guaranteed. Furthermore, the presence of the relatively leaktight protective enclosure avoids direct contact between the connective tissues and the material of the joint, reducing the risk of infection and malfunctioning of the prosthesis.

BRIEF DESCRIPTION OF THE FIGURES

Further features and advantages of the invention will be more apparent from the description of some preferred but not exclusive embodiments of a phalangeal endoprosthesis according to the invention, illustrated by way of a non-restrictive example with the help of the appended drawing sheets in which.

DESCRIPTION OF SOME PREFERRED EMBODIMENTS

With reference to the figures mentioned, a metacarpal-phalangeal or interphalangeal joint prosthesis indicated as a whole by the reference number 1 comprises generally two pins 2, 3 which extend from opposite sides of a connecting joint 4.

Figure 1:
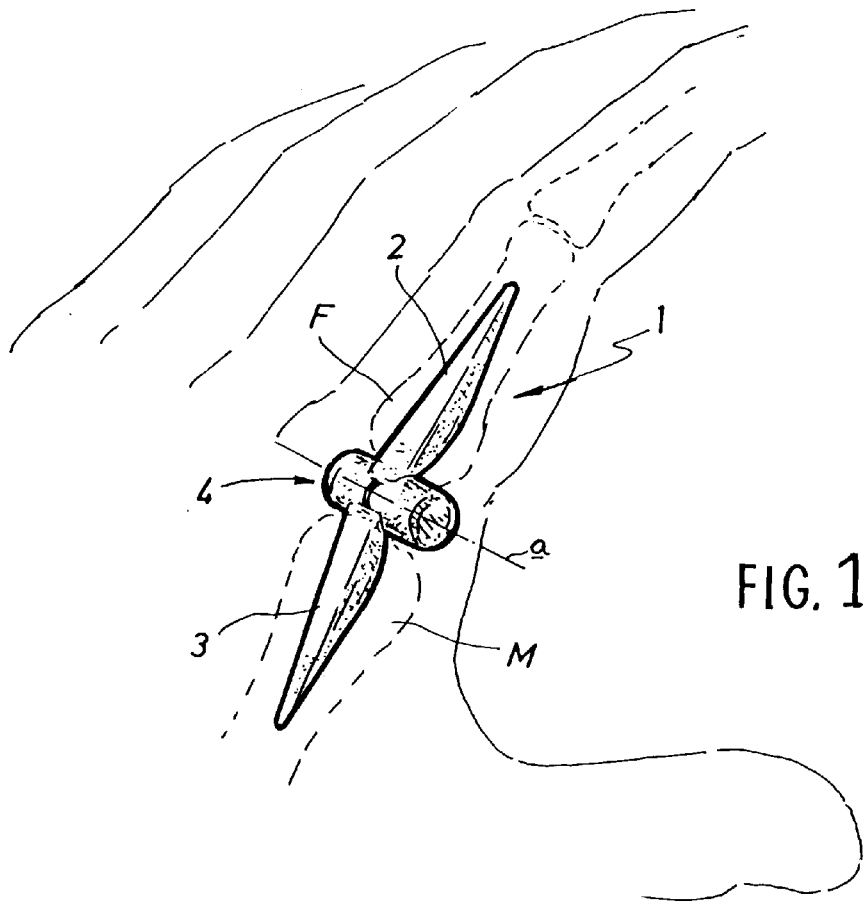
FIG. 1 shows a general perspective view of an endoprosthesis according to the invention implanted in a metacarpal-phalangeal joint of the hand.
Figure 2:
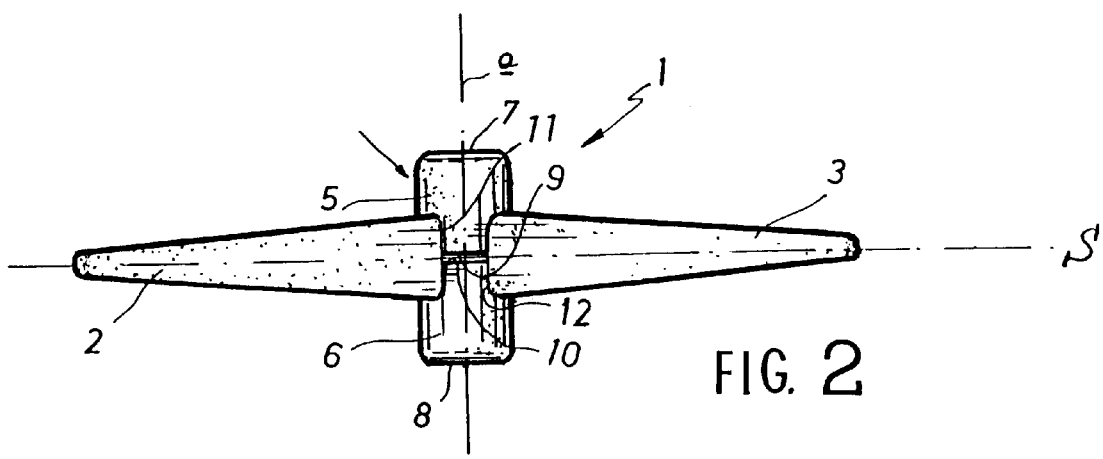
FIG. 2 illustrates a front view of the prosthesis in FIG. 1.

Pins 2, 3 have a shape which tapers towards the end with a slight convexity close to the joint. Because of this shape the pins can be inserted into longitudinal seats suitably constructed by the surgeon in the adjacent metacarpal bone M and phalangeal bone F, shown by dashed lines in FIG. 1.

Obviously the prosthesis could be implanted between two adjacent phalangeal bones, instead of between a metacarpal bone and a phalangeal bone, without this altering the fundamental features of the invention. It is also obvious that prostheses of different size could be provided to adjust to the size of patients and the implantation sites.

The pins may be housed in the seats with or without anchoring by means of bone adhesive or cement.

Joint 4 shows a hinge or pivot axis a transverse to the pins which permits appreciable mobility, avoiding excessive flexion of the joint.

According to the invention, pins 2, 3 are constructed of a material compatible with the bone tissue of the joint. In particular, the basic material of the pins may comprise the same bone cement used to anchor the pins in the bone seats, which is a material which has been used in orthopaedics for more than 40 years.

Preferably, the biocompatible material may be a two-component cement mixture in which the solid phase comprises a polymethyl methacrylate (PMMA) in powder form with spheroidal particles of differentiated particle size, and the liquid phase comprises a monomer and an accelerator.

Advantageously active and medicinally active components to encourage regeneration of the bone tissue may be present in the mixture. The cement mixture described and claimed in Italian patent no. 1,234,978 in the name of the applicant has proved particularly suitable for the purpose.

The pins may be formed using moulds into which the cement mixture is poured in the plastic state and then allowed to harden until the necessary consistency and rigidity is achieved.

The pins formed in this way will be perfectly compatible with bone tissue and with the layer of anchoring bone cement, and their basic material will be completely assimilated into the surrounding tissue. Thus the probabilities of infection and rejection typical of the known art will be reduced. In the course of the implant operation the pins can be perfectly matched to the seats by the surgeon, by gentle filing or similar procedures.

In a preferred embodiment the connecting joint 4 between pins 2, 3 is encapsulated in an almost hermetically sealed protective enclosure constructed using the same material as the pins.

Advantageously the shell may be formed of two opposing half-shells 5, 6 integral with corresponding pins 2, 3. These half shells 5, 6 extend on opposite sides with respect to a plane of symmetry S approximately perpendicular to the axis a of the joint.

Half shells 5, 6 may have a cylindrical shape with transverse base walls 7, 8 and opposing circular edges 9, 10 defining sealing surfaces lying in the said longitudinal plane of symmetry S.

Figure 3:
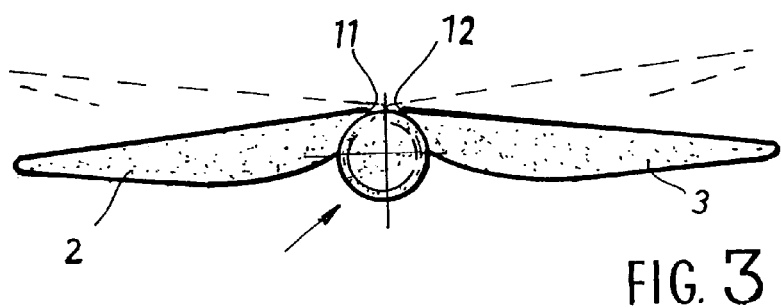
FIG. 3 shows a side view of the prosthesis in FIG. 1.

In the connection zone to the pins, half shells 5, 6 have projections 11, 12 which form abutment surfaces which restrict the relative rotation of the pins in the direction of extension of the phalanges to within a certain angle, as illustrated by the dashed line in FIG. 3. In the opposite direction rotation is not angularly limited and therefore complete flexion of the finger will be permitted.

The axis of rotation a of the joint coincides with that of a physical member housed in the two half shells capable of maintaining them joined together.

Figure 4:
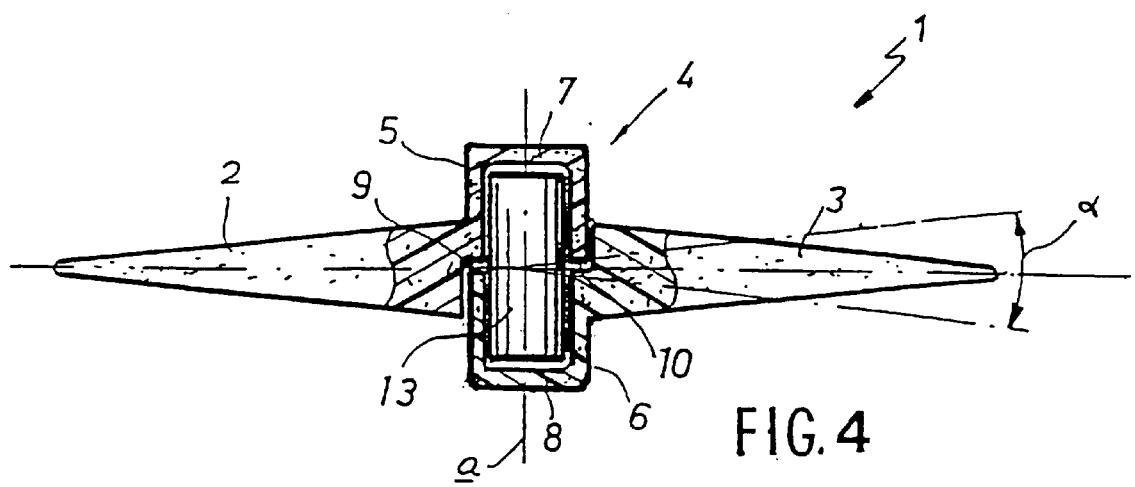
FIG. 4 shows a view in cross-section along an axial plane of a first embodiment or modification of the prosthesis in FIGS. 1 to 3.

FIG. 4 illustrates a first embodiment of the joint in which the physical member defining its axis comprises a metal pin 13, for example of stainless steel of type AISI316, having an external diameter which is slightly smaller than the internal diameter of the two half shells 5, 6. One of the two half shells may have an internal diameter which is slightly smaller than that of pin 13 so as to form a force-fit coupling with it, while the other will be slightly larger so as to form a precise free coupling with the said pin. In each case the two pins with their corresponding half shells will be held in the same axis with the possibility of oscillating in a plane perpendicular to the plane of rotation with an angle α having an amplitude of less than approximately 15° as illustrated by the dashed line in FIG. 4. The two pins will also be held axially by the surrounding tissue without any need for contact surfaces.

Figure 5:
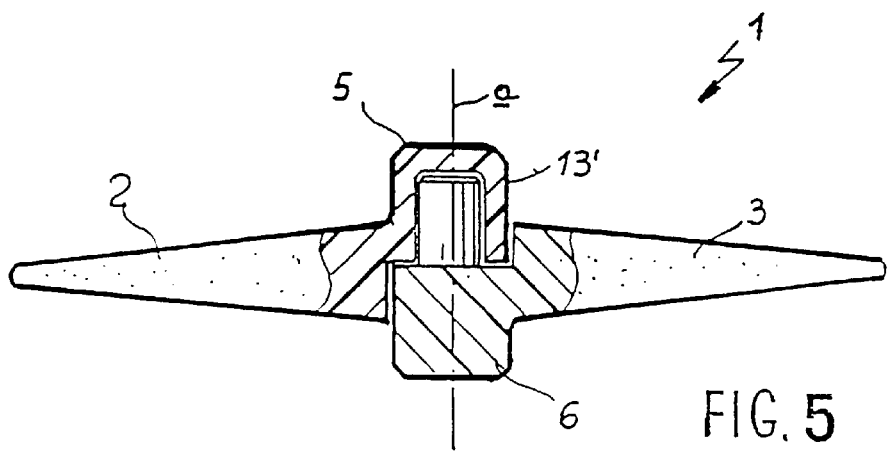
FIG. 5 shows a view in cross-section along an axial plane of a second embodiment of the prosthesis in FIGS. 1 to 3.

The second embodiment illustrated in FIG. 5 differs from the first in that the physical member defining the axis of rotation comprises a cylindrical extension 13' which is incorporated into pin 6 and is inserted into the corresponding cylindrical cavity in pin 5.

Figure 6:
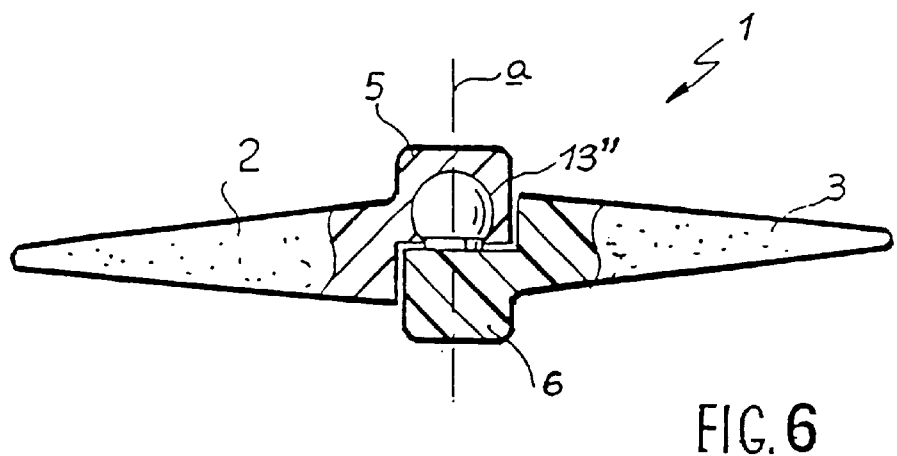
FIG. 6 shows a view in cross-section along an axial plane of a third embodiment of the prosthesis in FIGS. 1 to 3.

The third form of embodiment illustrated in FIG. 6 differs from the second in that extension 13" is of substantially spherical shape and is coupled elastically with a cavity of complementary shape formed in pin 5.

Figure 7:
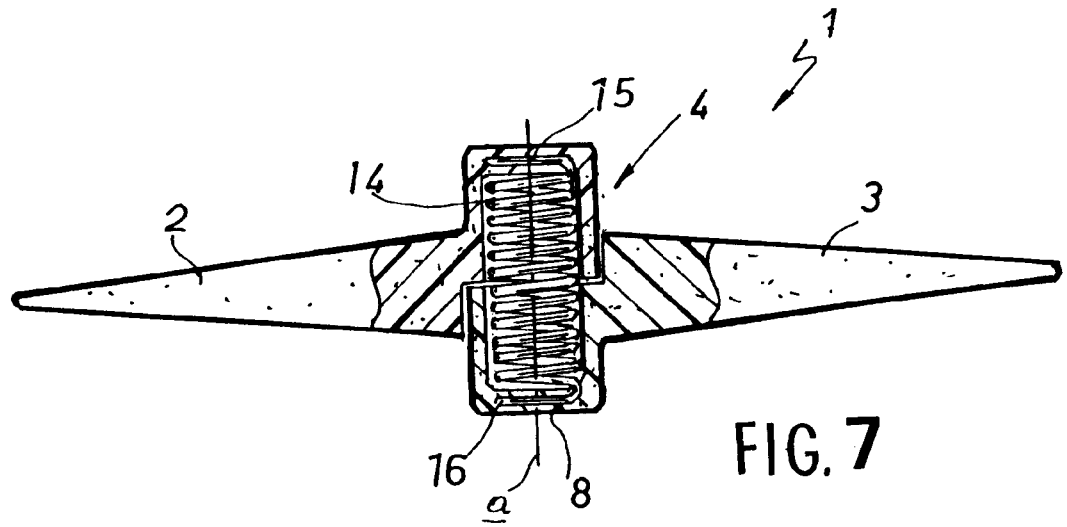
FIG. 7 shows a view in cross-section along an axial plane of a fourth embodiment of the prosthesis in FIGS. 1 to 3.

FIG. 7 illustrates a fourth embodiment in which the physical member defining the axis of rotation of the joint comprises a spring 14, preferably but not necessarily of a helicoidal type, with terminal portions 15, 16 embedded in the walls of the transverse bases 7, 8 of corresponding half shells 5, 6. Under resting conditions spring 14 has an axial length which is approximately equal to twice the depth of the cavities in the said half shells. Spring 14 exerts axial tension on the two half shells, increasing the seal along edges 9, 10, in such a way as to provide a mechanical barrier for the surrounding tissues.

In addition to this, spring 14 elastically opposes relative rotation of the half shells, and therefore the pins, helping to keep the finger extended. Here again slight flexion of the joint in a plane perpendicular to the plane of rotation is permitted.

Figure 8:
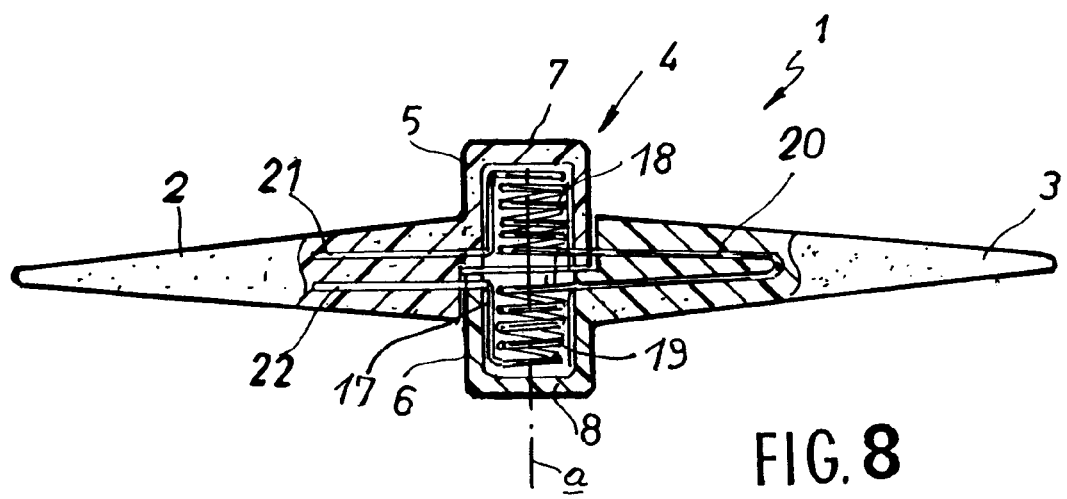
FIG. 8 shows a view in cross-section along an axial plane of a fifth embodiment of the prosthesis in FIGS. 1 to 3.

In the fifth embodiment illustrated in FIG. 8 a spring 17 is again present but this time it is not of one piece, but comprises two portions 18 and 19 spaced apart axially. These portions are joined by a straightened turn 20 pointing radially outwards and then folded back in a U-shape and finally embedded in pin 3. The outer ends of the two portions 21, 22 are extended and folded back forming first lengths which are directed axially inward connected to second lengths which are directed radially outward. The latter are embedded in the basic material of the other pin 2.

Figure 9:
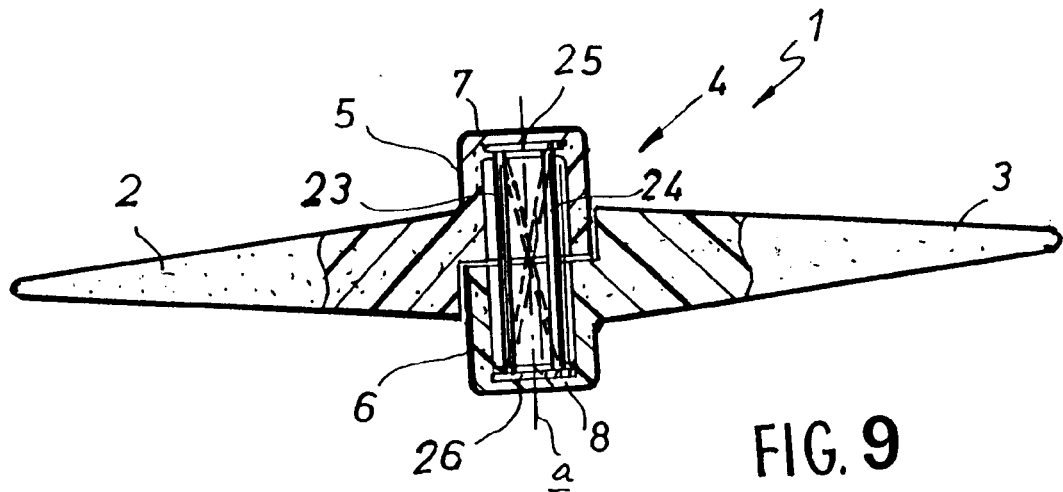
FIG. 9 shows a view in cross-section along an axial plane of a sixth embodiment of the prosthesis in FIGS. 1 to 3.

FIG. 9 illustrates a further embodiment of joint 4 in which the physical member defining the axis comprises a pair of wires 23, 24 which are turned and polished, joined together by two transverse end plates 25, 26 embedded in bottom walls 7, 8 of the half shells. In the resting condition wires 23, 24 are substantially parallel, but during rotation of the joint they twist as illustrated by the dashed line in FIG. 9, exerting an axial attractive force which tends to increase the seal at the circular edges 9, 10 of the half shells. The two wires may also be slightly prerotated to reduce the axial shortening effect when rotating in the opposite direction. As an alternative one of plates 25, 26 may be housed in the corresponding cavity with a small amount of play in the axial direction to allow it to approach without causing shortening of the axis and therefore stiffening of the joint.

Together, wires 23, 24 with end plates 25, 26 define an elastic member which is equivalent to a torsion bar, but which is extremely flexible and light.

In use the prosthesis is implanted with the pins inserted into the cavities of the metacarpal bone and/or phalanges, eliminating any problem of incompatibility and infection. Because the only metal parts are encapsulated in the enclosures formed by the opposing half shells, the probability of contact with the surrounding tissues and therefore the release of metals are reduced to a minimum.

Through the simplicity of its construction and the structural properties of the materials used the prosthesis according to the invention is extremely reliable and robust and has a relatively low cost, accomplishing all the objectives specified.

We claim:

1. A metacarpal-phalangeal or interphalangeal prosthesis, particularly for joints in the hand or foot, comprising two pins (2, 3) which can be inserted into bone adjacent to a joint to be restored, and a flexible joint (4) or coupling designed to join said pins to each other, said pins (2, 3) being constructed of a material which is biocompatible with the surrounding tissue, said joint (4) being substantially completely encapsulated in a protective enclosure, characterized in that said enclosure is formed of the same basic material as the pins (2, 3) and comprises a pair of opposing half shells (5, 6) integral with the corresponding pins (2, 3).

2. A prosthesis according to claim 1, characterized in that said biocompatible material is a mixture of hardening and biocompatible resin and plastics.

3. A prosthesis according to claim 2, characterized in that said mixture comprises a solid phase of a polymethyl methacrylate polymer combined with a liquid phase of a monomethyl-methacrylate monomer to form a hardening plastics resin.

4. A prosthesis according to claim 3, characterized in that said half shells (5, 6) extend axially from opposing sides with respect to a longitudinal plane of symmetry (S) which is substantially perpendicular to the axis of rotation (a) of the joint.

5. A prosthesis according to claim 4, characterized in that said half shells (5, 6) have a substantially cylindrical shape with transverse base walls (7, 8) and opposing circular edges (9, 10) defining sealing surfaces laying on the said plane of longitudinal symmetry (S).

6. A prosthesis according to claim 5, characterized in that said half-shells (5, 6) have abutment surfaces (11, 12) adapted to limit the relative rotation of the pins in the direction corresponding to extension of the phalanges.

7. A prosthesis according to claim 6, characterised in that said abutment surfaces (11, 12) comprise projections formed in the area of connection between the said pins (2, 3) and the corresponding half shells (5, 6).

8. A prosthesis according to claim 5, characterised in that the axis of rotation (a) of the joint is defined by a cylindrical pin (13) inserted in the axial cavities of the said half shells (5, 6) which is free to rotate with respect to at least one of these with limited flexibility in a plane perpendicular to the said axis of rotation (a).

9. A prosthesis according to claim 5, characterised in that the said axis of rotation (a) is defined by a substantially cylindrical extension (13') from one of the said half shells (6) inserted into a correspondingly shaped cavity formed in the other (5) of the said half shells (5).

10. A prosthesis according to claim 5, characterised in that the said axis of rotation (a) is defined by a substantially hemispherical extension (13") from one of the said half shells (6) inserted into a cavity of complementary shape formed in the other (5) of the said half shells.

11. A prosthesis according to claim 5, characterised in that the said axis of rotation (a) is defined by the axis of a spring (14) placed within the axial cavities of the said half shells (5, 6).

12. A prosthesis according to claim 11, characterised in that the said spring (14) has an axial length approximately equal to twice the depth of the cavities in the said half shells, and has distal ends (15, 16) which are anchored in their corresponding base walls (7, 8).

13. A prosthesis according to claim 11, characterised in that the said spring (17) is divided into two axially separated portions (18, 19) joined by an intermediate section (20) which is bent into a "U" shape and directed radially outwards with respect to the axis of the joint.

14. A prosthesis according to claim 13, characterised in that the said intermediate section (20) which is folded into a "U" shape is at least partially embedded in the basic material of one (3) of the said pins.

15. A prosthesis according to claim 14, characterised in that the two portions (18, 19) of the axially separated spring have, at their distal ends first lengths of wire directed axially towards the plane of symmetry of the joint connected to second lengths of wire directed radially outwards with respect to the axis of the joint, with the said lengths (21, 22) at least partially embedded in the other of the said pins.

16. A prosthesis according to claim 11, characterised in that the said axis of rotation is defined by the distance between centres of at least one pair of wires (23, 24) which are substantially parallel or slightly prerotated, said wires having longitudinal ends coupled to two transverse plates (26, 26) anchored in the corresponding transverse walls (7, 8) of the said half shells (5, 6).

17. A prosthesis according to claim 16, characterised in that at least one of the said plates (25) is housed with minimum axial play in a cavity of the said base wall (7) of the half shell in which it is anchored.

* * * * *